United States Patent [19]

Burger et al.

[11] Patent Number: 4,948,578

[45] Date of Patent: Aug. 14, 1990

[54] TRANSPARENT ANTIPERSPIRANT STICK COMPOSITIONS

[75] Inventors: Allan R. Burger, Passaic, N.J.; Phillip E. Figdore, York, Pa.; Samuel Q. S. Lin, Paramus; Michael Massaro, Bogota, both of N.J.

[73] Assignee: Lever Brothers Company, New York, N.Y.

[21] Appl. No.: 355,097

[22] Filed: May 12, 1989

Related U.S. Application Data

[63] Continuation-in-part of Ser. No. 50,607, May 15, 1987, abandoned.

[51] Int. Cl.$^5$ .......................... A61K 7/34; A61K 7/38
[52] U.S. Cl. ............................... 424/68; 424/DIG. 5; 424/66
[58] Field of Search ..................... 424/66, 68, DIG. 5

[56] References Cited

U.S. PATENT DOCUMENTS

| | | | |
|---|---|---|---|
| 3,259,545 | 7/1966 | Teller | 424/68 |
| 3,472,940 | 10/1969 | Osipow et al. | 424/68 |
| 4,126,679 | 11/1978 | Davy et al. | 424/68 |
| 4,229,432 | 10/1980 | Gina | 424/68 |
| 4,264,586 | 4/1981 | Callingham et al. | 424/68 |
| 4,265,878 | 5/1981 | Keil | 424/68 |
| 4,268,499 | 5/1981 | Keil | 424/68 |
| 4,425,328 | 1/1984 | Nabial | 424/68 |
| 4,431,837 | 2/1984 | Geria | 424/68 |
| 4,499,069 | 2/1985 | Krafton | 424/66 |
| 4,511,554 | 4/1985 | Geria et al. | 424/65 |
| 4,518,582 | 5/1985 | Schamper et al. | 424/68 |
| 4,719,103 | 11/1988 | Krevald et al. | 424/DIG. 5 |

*Primary Examiner*—Dale R. Ore
*Attorney, Agent, or Firm*—Milton L. Honig

[57] ABSTRACT

An antiperspirant composition is disclosed in the form of a transparent stick. The composition comprises a mixture of aluminum chlorohydrate, nonionic surfactant, liquid oil, and water, the latter being present in an amount from 20 to 50%. Preferably, the liquid oil is a combination of volatile silicone and emollient oil.

17 Claims, No Drawings

TRANSPARENT ANTIPERSPIRANT STICK COMPOSITIONS

This is a continuation-in-part application of Ser. No. 050,607, filed May 15, 1987 now abandoned.

BACKGROUND OF THE INVENTION

1. Field of the Invention

The invention relates to an antiperspirant in the form of a transparent gelled stick.

2. The Prior Art

Solid antiperspirant formulations generally fall within two broad categories—suspensoid sticks and gelled alcoholic sticks. Suspensoid sticks usually consist of acidic antiperspirant actives suspended in a matrix formed by a wax in an emollient. Illustrative of this category are the formulations presented in U.S. Pat. No. 4,431,837 (Geria). Example 7 of this patent describes an antiperspirant stick suspending Rezal (aluminum/zirconium tetrachlorhydrex glycine complex) in a wax matrix of stearyl alcohol and Castorwax MP 80 Volatile silicone and $C_8$–$C_{18}$ aliphatic hydrocarbon ethoxylated alcohol benzoates are included as emollients and vehicles for the composition. See also U.S. Pat. No. 4,126,679 (Davy et al.). Unfortunately, these sticks cannot be formulated into an attractive transparent appearance. The wax matrix and insolubility of the antiperspirant active render the stick opaque.

Gelled alcoholic sticks may be formulated in either of two ways. One method is to utilize an alkaline aluminum chlorhydrate-lactate complex as the active and combine this with sodium stearate as a gelling agent. For instance, U.S. Pat. No. 3,259,545 (Teller) reports a stick containing an aluminum antiperspirant active, sodium lactate and sodium stearate. U.S. Pat. No. 3,472,940 (Osipow et al.) obtains stable gelled alcoholic compositions through the use of sodium stearyl-2-lactylate. A second method for obtaining gelled alcoholic sticks involves use of an alcohol soluble aluminum chlorhydrate complex (e.g. an aluminum chlorhydrate-propylene glycol adduct) and dibenzaldehyde monosorbitol acetal as gelling agent. Illustrative is U.S. Pat. No. 4,518,582 (Schamper et al.) wherein solid transparent gelled sticks of the foregoing type are disclosed.

Although gelled alcoholic sticks in transparent form can be achieved, these formulations suffer certain disadvantages. The alkaline aluminum active-lactate complex with sodium stearate is not particularly effective because alkaline antiperspirant actives intrinsically have low efficacy. Alcohol soluble aluminum active complexes as found in Schamper et al. provide unstable sticks because of the instability of acetal gelling agents in the presence of acidic aluminum actives. Many of the foregoing compositions form sticks that are not completely hardenable, thereby resulting in a tacky feel.

Accordingly, it is an object of the present invention to obtain an antiperspirant composition in stick form having improved antiperspirant properties and physical characteristics.

In particular, it is an object of the present invention to obtain a stick that is transparent and exhibits improved antiperspirancy.

Another object of the present invention is to obtain a transparent stick of acceptable hardness to avoid a tacky feel when applied to skin.

SUMMARY OF THE INVENTION

An antiperspirant composition in the form of a transparent stick which is an oil-in-water emulsion is provided comprising:

(i) from 5 to 25% of an antiperspirant effective aluminum salt;
(ii) from 10 to 40% of a nonionic surfactant which is a $C_{11}$–$C_{18}$ fatty alcohol alkoxylated with from about 10 to about 20 moles ethylene oxide;
(iii) from 5 to 50% of a liquid oil immiscible with water; and
(iv) from 20 to 50% water, and wherein said composition is free of any wax matrix.

Aluminum chlorhydrate is most desirable as the antiperspirant salt. The nonionic surfactant is, desirably, a $C_{11}$–$C_{18}$ alcohol ethoxylate. The liquid oil component may be selected from emollient oils, volatile silicones and, desirably, mixtures of these materials.

DETAILED DESCRIPTION OF THE INVENTION

It has been discovered that acidic aluminum antiperspirant salts may be structured into a clear stick form by use of nonionic surfactants. The basic composition comprises an oil-in-water emulsion, the water phase containing the active, aluminum chlorhydrate. Nonionic surfactant induces gelation to harden the composition. Transparency is achieved by matching the refractive indices of the two phases. Adjustment of refractive index is best performed with respect to the oil phase. Thus, volatile silicones are utilized in the oil phase to detackify the stick. Normally, there is a significant difference in the refractive index of silicone and water phases. An emollient oil, it has been found, may be added to the silicone for adjustment to compatibilize refractive indices of oil and water phases.

Unlike much of the known art, compositions of the present invention are free of any wax matrix normally employed to solidify the prior art products. The present invention does not include components such as stearyl alcohol or hydrocarbon waxes. Transparent sticks are undesirably opacified by the waxy elements.

The term "transparent" as used in this specification is intended to connote its usual dictionary definition. Thus, a transparent antiperspirant stick, like glass, allows ready viewing of objects behind it. By contrast, a translucent antiperspirant stick, although allowing light to pass through, causes the light to be so scattered that it will be impossible to clearly identify objects behind the translucent stick.

Within the context of this invention, an antiperspirant stick is deemed to be transparent if the maximum transmittance of light of any wavelength in the range 400 to 800 nm through a sample 1 cm thick is greater than 35%, but preferably at least 50%. A bar is deemed translucent if the maximum transmittance of such light through the sample is between 2% and less than 35%. Finally, a bar is deemed opaque if the maximum transmittance of such light is less than 2%. This transmittance can be easily measured by placing a stick sample of the required thickness into the light beam path of a UV-VIS spectrophotometer such as a Bausch & Lomb Spectronic 88 Spectrophotometer.

Antiperspirant actives suitable for the present invention include astringent acidic aluminum compounds, especially aluminum chlorhydroxides. Among the effective actives are aluminum chlorhydrate, activated aluminum chlorhydrate (Reach 201, sold by the Reheis Company), as well as lower aluminum/chlorine ratio actives (e.g. dichlorohydrates and sesquichlorohydrates). These actives will usually be present from about 5 to 25%, most preferably from about 10 to 20%. Beyond 20% active, the composition becomes more tacky and the stick softer. Unexpectedly, zirconium containing actives cause the composition to lose transparency. Thus, materials such as Rezal ® 36GP, Rezal ® 36 and Rezal ® 67P were found unsuitable. These actives appear to be strong salting out electrolytes for the surfactant.

Surfactants of the present invention must be capable of forming clear or translucent ordered liquid crystalline phases in the presence of water. Particularly desirable are surfactants forming viscous isotropic (cubic) and middle (hexagonal) phases. There must be no interaction between the surfactant and the antiperspirant actives in a manner leading to precipitation. For instance, anionic and amphoteric surfactants are unsuitable with the present compositions because of their incompatibility with the antiperspirant actives. Anionics and amphoterics, such as betaines, interact with the positively charged aluminum salts and thereby form a precipitating complex. By contrast, nonionic surfactants have been found not to adversely interact with the actives. These materials are also preferred because of their less irritating nature to the skin.

Nonionic surfactants particularly suitable for the present invention are alkoxylated $C_{11}$-$C_{22}$ fatty alkyl hydrophobes. Two categories of these type of materials are particularly effective. These are:

(a) polyoxyethylene and/or polyoxypropylene condensates of aliphatic carboxylic acids, whether linear- or branched-chain and unsaturated or saturated, containing from about 11 to about 22 carbon atoms in the aliphatic chain and incorporating from about 7 to about 40 ethylene oxide or propylene oxide units. Suitable carboxylic acids include "coconut" fatty acid which contains an average of about 12 carbon atoms, "tallow" fatty acid which contains an average of about 18 carbon atoms, palmitic acid, myristic acid, stearic acid and lauric acid.

(b) polyoxyethylene and/or polyoxypropylene condensates of aliphatic alcohols, whether linear- or branched-chain and unsaturated or saturated, containing from about 11 to 22 carbon atoms and incorporating from about 7 to 40 ethylene oxide and/or propylene oxide units. Suitable alcohols include the "coconut" fatty alcohol, "tallow" fatty alcohol, lauryl alcohol, myristic alcohol, and oleyl alcohol.

Most effective within the context of this invention are the $C_{11}$-$C_{18}$ fatty alcohols ethoxylated with from about 10 to about 20 moles ethylene oxide. Especially effective, and studied in detail, is Neodol ® 45-13 which is a $C_{14}$-$C_{15}$ fatty alcohol ethoxylated with 13 moles of ethylene oxide. Further preferred nonionic surfactants are Brij 99, a $C_{18}$ fatty alcohol alkoxylated with 20 moles ethylene oxide, and Ceteth 16, a $C_{16}$ fatty alcohol alkoxylated with 16 moles ethylene oxide.

Amounts of the nonionic surfactant required for the compositions of this invention range from about 10 to 40%, preferably from about 25 to 35% by weight.

The compositions of the present invention must contain a liquid oil immiscible with water. Total liquid oil present will range from about 5 to about 50% by weight, preferably from about 10 to 40% by weight. The liquid oil component may itself be composed of emollient oils, volatile silicones, and preferably mixtures thereof. Emollient oils are defined as liquids at room temperature being immiscible with water (and preferably miscible with volatile silicones). Among the emollient oils may be included linear and branched chain fatty acid esters, diesters of dicarboxylic acids, and liquid hydrocarbons. Examples of fatty acid esters include the isopropyl esters of myristic, palmitic and stearic acids. Branched chain fatty acid esters are illustrated by 2-butylhexylpalmitate and 2-ethylhexyloxystearate. Di-n-butyl phthalate and diisopropyladipate are exemplative of dicarboxylic acid diesters. Mineral oils and paraffins, such as Isopar ® from Exxon, are illustrative of suitable liquid hydrocarbons. Most preferred among the emollient oils is 2-ethylhexyloxystearate which is available as Wickenol 171 from the Wickhen Corporation. Emollient oil will usually be present from about 2 to 30%, preferably from about 5 to 15% by weight of the composition.

Volatile silicones are present mainly to assist in detackifying the stick. These materials also provide a dry, non. oily lubricant effect when stick contacts skin. Volatile silicones are relatively low molecular weight cyclic siloxane oligomers. The most readily available species of these siloxanes are hexamethylcyclotrisiloxane (boiling point 134° C.), octamethylcyclotetrasiloxane (boiling point 175.8° C.) and decamethylcyclopentasiloxane (boiling point 210° C.), more commonly known as trimer ($D_3$), tetramer ($D_4$) and pentamer ($D_5$), respectively. Under CTFA terminology, the $D_4$ and $D_5$ materials are identified as cyclomethicone. Commercially the $D_5$ cyclomethicone is available from Union Carbide Corporation as VS7158 and as DC 344 from Dow Corning Corporation. Amounts of volatile silicone in the present compositions will range from about 5 to 30%, preferably from about 10 to 20% by weight.

Although volatile silicone can be utilized as the only component of the liquid oil phase, often there is a problem with matching the refractive indices of volatile silicone with the aqueous phase and other components of the composition. Therefore, it has been found useful to substitute a portion of the volatile silicone with an appropriate emollient oil for adjustment of refractive index. When combinations of a volatile silicone and emollient oil are utilized, the ratios of these materials will range from about 10:1 to 1:10, respectively. Preferably, the respective ratio will range from about 4:1 to 1:4, optimally about 2:1 to 1:1.

It is recognized that for a given surfactant level, cosmetic properties of the stick, such as its hardness and tackiness, are dependent on both the nature and level of the oil phase. In general, as the oil level increases, the stick becomes less tacky. However, hardness will increase initially but then decrease as the oil level is further increased.

Water is an important component of the composition. It must be present from about 20 to 50% by weight of the composition, preferably from about 25 to about 35% by weight. Amounts substantially lower than about 20% water result in sticks that are quite poor in hardness.

Other optional ingredients may be incorporated into the compositions of this invention. These ingredients include perfumes, preservatives, colorants and antimicrobial deodorizing agents (e.g. triclosan). These materials will usually be present each in amounts less than 5%, and usually less than 1%.

Antiperspirant sticks of the present invention may be prepared by either of four methods. A "normal" addition method involves adding the oily phase slowly to the surfactant dissolved in the aqueous antiperspirant active containing mixture. "Reverse addition" may also be practiced wherein the aqueous antiperspirant active combination is added to a mixture of surfactant and oily phase. Thirdly, it is possible to add surfactant to an emulsion of the water phase containing antiperspirant active with the oily phase. Finally, it is possible to add the emulsion of oily phase and aqueous phase containing active antiperspirant to the surfactant. Although all four methods are operative, the "reverse addition" procedure has mainly been utilized because of its simplicity and lower degree of foaming relative to, for instance, the "normal addition" method.

The following examples will more fully illustrate the embodiments of this invention. All parts, percentages and proportions referred to herein and in the appended claims are by weight unless otherwise indicated.

EXAMPLE 1

Illustrative of a typical preparation is that described as follows: Neodol ® 45-13, in the amount of 33 grams, was added to a thermostatted beaker maintained at 65-75° C. A mixture was prepared of 17 grams water with 30 grams of a 50% aqueous aluminum chlorohydrate solution. The combined water and aluminum chlorohydrate was then slowly added to the Neodol ® 45-13 with constant gentle agitation using a magnetic stirrer. Slow stirring was continued until most of the bubbles had dissipated. Refractive index of the solution was then measured. Thereafter, a mixture was prepared of 12.8 grams VS 7158 (volatile silicone) and 7.2 grams Wickenol 171 (2-ethylhexyloxystearate). Refractive index of the oil phase was now measured. In those instances where the oil and water phases were not within approximately 0.001 units refractive index from one another, the ratio of VS 7158:Wickenol 171 was readjusted by an increase in the appropriate oil to attain the equivalent refractive index. Next, the oil phase was slowly added with stirring to the surfactant/water/active phase. When most of the bubbles had dissipated, the composition was poured into molds to cool.

EXAMPLES 2-6

A series of further compositions were prepared by the method outlined in Example 1. These compositions were used to evaluate the effect of volatile silicone and emollient oils.

TABLE I

Effect of Volatile Silicone and Emollient Oil

| Ingredient | Example (Parts by Weight) | | | | |
|---|---|---|---|---|---|
| | 2 | 3 | 4 | 5 | 6 |
| Neodol ® 451-13 | 33 | 33 | 33 | 32 | 32 |
| Water | 32 | 32 | 31.96 | 33 | 33 |
| Aluminum Chlorohydrate | 15 | 15 | 15 | 10 | 10 |
| VS7158 | 12.8 | 19* | 12.8 | 16 | 19 |
| Wickenol 171 | 7.2 | — | 7.2 | 9 | — |
| Perfume | — | 1 | — | — | — |
| FD & C Blue #1 | — | — | .04 | — | — |
| Finsolv TN | — | — | — | — | 6 |

*Total VS7158 + Wickenol 171 = 19%; exact ratio of VS7158 to Wickenol 171 will depend on the refractive index of the perfume.

Examples 2 and 3, respectively, illustrate how the stick may be perfumed or dyed. A decrease in antiperspirant active level and an increase in the oil level was found to result in a less tacky product. Compare Examples 2 and 5. Example 6 is similar to that of 5 but illustrates the use of a different oil to adjust the oil phase refractive index. All Examples provided transparent compositions.

EXAMPLES 7-11

A composition identical to that of Example 1 was prepared but using the "reverse addition" method. All components of the oil phase were mixed and this was added slowly with stirring to the surfactant. Next, the antiperspirant active/water solution was slowly added to the surfactant/oil phase. The resultant emulsion was allowed to stand until the bubbles had dissipated. Compositions made thereby were then poured into molds. "Reverse addition" resulted in less foam and bubble problems than occurred in Example 1. The formulations prepared according to this method are outlined in Table II.

TABLE II

| Ingredient | Example (Parts by Weight) | | | | |
|---|---|---|---|---|---|
| | 7 | 8 | 9 | 10 | 11 |
| Neodol 45-13 | 33 | 30 | 33 | 16.5 | — |
| Water | 32 | 32 | 32 | 32 | 33 |
| Aluminum Chlorohydrate | 15 | 20 | 15 | 15 | 15 |
| VS7158 | 12.8 | 10.8 | 20 | 20* | 20* |
| Wickenol 171 | 7.2 | 7.2 | — | — | — |
| Isosteareth 20 | — | — | — | — | 32 |
| BRIJ 78 | — | — | — | 16.5 | — |

*Exact composition will vary according to transparency requirements.

Example 8, relative to that of 7, contains an increased level of antiperspirant active and decreased level of oil; the stick derived from Example 8 was more tacky than that of Example 7. The product of Example 9 was not transparent due to the mismatch of refractive indices of the phases. Examples 10 and 11 illustrate the use of mixed surfactants and a surfactant other than Neodol ® 45-13. Examples 7, 8, 10 and 11 were transparent.

EXAMPLES 12-26

Formulation effects upon stick hardness are illustrated in the following examples. In all cases, the oil phase was a mixture of VS 7158:Wickenol 171 (64:36).

TABLE III

Formulation Effects Upon Stick Hardness

| Example | % Neodol ® 45-13 | % Aluminum Chlorohydrate | % Water | % Oil | Relative Hardness |
|---|---|---|---|---|---|
| 12 | 22 | 15 | 22 | 41 | 0.30 |
| 13 | 24 | 15 | 24 | 37 | 0.39 |
| 14 | 28 | 15 | 47 | 10 | 0.48 |
| 15 | 28 | 15 | 37 | 20 | 0.63 |
| 16 | 28 | 15 | 27 | 30 | 0.44 |
| 17 | 28 | 15 | 22 | 35 | 0.30 |
| 18 | 31 | 15 | 34 | 20 | 0.89 |
| 19 | 33 | 15 | 47 | 5 | 0.41 |
| 20 | 33 | 15 | 42 | 10 | 0.89 |
| 21 | 33 | 15 | 37 | 15 | 1.00 |
| 22 | 33 | 15 | 32 | 20 | 1.00 |
| 23 | 33 | 15 | 25 | 27 | 0.63 |
| 24 | 33 | 15 | 14 | 38 | 0.04 |
| 25 | 35 | 15 | 40 | 10 | 1.33 |
| 26 | 35 | 15 | 30 | 20 | 0.89 |

Stick hardness was measured using an Instron Model 1122 Universal Testing Instrument, employing an 8.9 mm penetrometer driven at 2 mm/minute.

Examples 14–17 and 19–24 illustrate, respectively, the effect of oil level upon hardness at 28 and 33% surfactant. Maximum hardness occurs at both surfactant levels around the 20% oil level. Other Examples in Table III investigate hardness values at levels lower and higher than the 28–33% surfactant concentration. Generally, hardness increases in direct proportion to the surfactant level. For instance, compare Example 14, 20 and 25 where the oil level is constant at 10% and surfactant is investigated at 28, 33 and 35%, respectively. Relative hardness increases from 0.48 up to 1.33 as the surfactant is increased.

Examples 25 and 26 show that optimum hardness can occur at different levels of oil depending on the surfactant concentration. For instance, Example 25 (10% oil) is harder than that of Example 26 (20% oil) at the 35% surfactant level. By contrast at 33% surfactant level, the 10% oil formulation of Example 20 is softer than the 20% oil formulation of Example 21.

EXAMPLES 27–40

The following Examples illustrate the use of different types of nonionic surfactants and their effect upon relative hardness. All of the formulations contained 33% surfactant, 15% aluminum chlorohydrate, 32% water and 20% VS 7158/Wickenol 171 as the oil phase. Table IV outlines these formulations:

TABLE IV
Effect of Various Surfactants on Stick Hardness

| Example | Surfactant | CTFA Name | No. of C atoms in Fatty Alcohol | No. of EO Groups | Relative Hardness |
| --- | --- | --- | --- | --- | --- |
| 27 | Procol LA20 | Laureth 20 | 12 | 20 | 0.55 |
| 28 | Siponic TD 990 | Trideceth 9 | 13 | 9 | 0.09 |
| 29 | Macol TD 10 | Trideceth 10 | 13 | 10 | 0.19 |
| 30 | Renex 30 | Trideceth 12 | 13 | 12 | 0.27 |
| 31 | Neodol ® 45-13 | Pareth 45-13 | 14–15 | 13 | 1.00 |
| 32 | Tergitol 15-S-20 | Pareth 15-20 | 11–15 | 20 | 0.37 |
| 33 | Brij 56 | Ceteth 10 | 16 | 10 | 0.41 |
| 34 | Procol CA16 | Ceteth 16 | 16 | 16 | 0.85 |
| 35 | Procetyl AWS | PPG5-Ceteth 20 | 16 | 20* | 0.44 |
| 36 | Procol CS-20 | Cetereth 20 | 16/18 | 20 | 0.52 |
| 37 | Brij 76 | Steareth 10 | 18 | 10 | 0.06 |
| 38 | Arosurf 66E10 | Isosteareth 10 | 18 (iso) | 10 | 0.55 |
| 39 | Brij 97 | Oleth 10 | 18 (oleyl) | 10 | 0.48 |
| 40 | Brij 99 | Oleth 20 | 18 (oleyl) | 20 | 0.76 |

*Co-alkoxylated with 5 propylene oxide groups.

From Table IV, it appears that most $C_{11}$–$C_{18}$ alcohol ethoxylates impart some degree of hardness to the stick. It is, however, noted that Neodol ® 45-13, Procol CA16 and Brij 99 are particularly effective.

EXAMPLES 41–59

In these Examples there are illustrated surfactants which do not result in a hard material; liquid phase or soft gels were obtained with these surfactants. Again, all of the formulations contain 33% surfactant, 15% aluminum chlorhydrate, 32% water and 20% VS 7158/Wickenol 171 as the oil phase. Table V outlines the ineffective surfactants.

TABLE V
Surfactants Not Providing Hard Sticks

| Example | Surfactant | CTFA Name | No. Carbons In Hydrophobe Group | No. of EO Groups |
| --- | --- | --- | --- | --- |
| 41 | Sandoz SX-408 | Pending* | 10 (iso) | 4 |
| 42 | Sandoz SX-412 | Pending* | 10 (iso) | 6 |
| 43 | Sandoz SX-418 | Pending* | 10 (iso) | 9 |
| 44 | Sandoz SX-424 | Pending* | 10 (iso) | 12 |
| 45 | Brij 721 | Steareth 21 | 18 | 21 |
| 46 | Triton X-100 | Octoxynol 9 | — | 9 |
| 47 | Tergitol 24-L-25N | Pareth-25 | 12–14 | 25 |
| 48 | Tergitol 24-L-35N | Pareth-35 | 12–14 | 35 |
| 49 | Tergitol 24-L-50N | Pareth-50 | 12–14 | 50 |
| 50 | Polychol 20 | Laneth 20 | — | — |
| 51 | Emerest 2712 | PEG-8-distearate | — | — |
| 52 | Emerest 2715 | PEG-40-distearate | — | — |
| 53 | Mapeg CO25H | PEG-25 Hydrogenated | — | — |
| 54 | Barlox 14 | Myristamine Oxide | — | — |
| 55 | Schercomid CCD | Cocamide DEA | — | — |
| 56 | Carsamide CMEA | Lauramide DEA | — | — |
| 57 | Lonzaine CZ | Cocoamidosulfo-betaine | — | — |
| 58 | Pluronic F127 | Poloxamer 407 | — | — |

TABLE V-continued

Surfactants Not Providing Hard Sticks

| Example | Surfactant | CTFA Name | No. Carbons In Hydrophobe Group | No. of EO Groups |
|---|---|---|---|---|
| 59 | Pluronic L72 | Poloxamer 212 | — | — |

*These surfactants contain 2 propylene groups in addition to the ethylene oxide groups on the $C_{10}$ alkyl chain.

EXAMPLES 60-73

The following Examples illustrate the effect of various liquid oils on the properties of the stick as described in Example 1. All formulations contain 33% Neodol ® 45-13, 15% aluminum chlorohydrate, 32% water and 20% of the oil phase. These formulations were not adjusted to transparency, but merely formulated to achieve adequate hardness.

TABLE VI

Effect of Various Liquid Oils

| Example | Oil | Relative Hardness |
|---|---|---|
| 60 | Volatile Silicone 7158 | 0.52 |
| 61 | 2-Ethylhexyloxystearate | 0.70 |
| 62 | 64:36, Volatile Silicone 7158:2-ethylhexyloxystearate | 1.00 |
| 63 | Isopropyl Palmitate | 1.04 |
| 64 | Isopropyl Myristate | 0.9 |
| 65 | Isopropyl Stearate | 1.1 |
| 66 | Butyl Myristate | 0.85 |
| 67 | 2-Ethylhexyl Palmitate | 1.00 |
| 68 | 2-Ethylhexyl Stearate | 1.2 |
| 69 | Isopar C ($C_7$–$C_8$ isoparaffin, bp 99° C.) | 0.96 |
| 70 | Isopar M ($C_{13}$–$C_{14}$ isoparaffin, bp 223° C.) | 1.07 |
| 71 | $C_{12}$–$C_{15}$ Benzoate (Finsolv TN) | 0.15 |
| 72 | Myristyl Octanoate | 0.85 |
| 73 | Di-2-ethylhexyl Succinate | 0.63 |

EXAMPLE 74

In this Example, the effect of zirconium containing actives are evaluated. A composition containing 14 grams aluminum chlorohydrate, 33 grams Neodol ® 45-13 and 32 grams water was formulated with 1 gram of a zirconium/aluminum antiperspirant active. The results are recorded in Table VII. It is evident that the presence of zirconium renders the composition non-transparent.

TABLE VII

Effect of Zirconium/Aluminum Active on Transparency

| Antiperspirant Active | A | B | C | D |
|---|---|---|---|---|
| Aluminum Chlorohydrate | 15 | 14 | 14 | 14 |
| Rezal 36GP* | — | 1 | — | — |
| Rezal 36* | — | — | 1 | — |
| Rezal 67GP* | — | — | — | 1 |
| Appearance | | | | |
| Clarity | Clear | Cloudy | Cloudy | Cloudy |

*Contains Zirconium as part of the active system.

EXAMPLE 75

Herein is illustrated the differences in clarity between different stick formulations. Clarity was determined by measuring the transmittance of a 1.0 cm thick section of a stick formulation by use of a Bausch & Lomb Spectronic 88 Spectrophotometer. Table VIII sets forth a pair of formulations, one transparent and the other translucent. These formulations were then measured for transmittance and compared with a commercial opaque stick.

TABLE VIII

Formulations Measured for Transmittance

| Ingredient | Transparent Formula Weight % | Translucent Formula Weight % |
|---|---|---|
| Neodol 45-13 | 33.0 | 33.0 |
| VS 7158 | 12.8 | 10.0 |
| Wickenol 171 | 7.2 | 10.0 |
| Aluminum Chlorohydrate | 15.0 | 15.0 |
| $H_2O$ | 32.0 | 32.0 |

TABLE IX

Transmittance Values of Antiperspirant Stick Formulations

| Wavelength (nm) | Transparent Formulation (Transmittance %) | Translucent Formulation (Transmittance %) | Opaque Commercial Stick (Transmittance %) |
|---|---|---|---|
| 400 | 48.0 | 2.5 | 0 |
| 450 | 50.0 | 3.5 | 0 |
| 500 | 52.0 | 5.0 | 0 |
| 550 | 54.0 | 6.0 | 0 |
| 600 | 57.5 | 7.5 | 0 |
| 650 | 61.0 | 9.5 | 0 |
| 700 | 65.5 | 11.0 | 0 |
| 750 | 69.0 | 12.5 | 0 |
| 800 | 73.0 | 14.0 | 0 |

The foregoing description and examples illustrate selected embodiments of the present invention and in light thereof variations and modifications will be suggested to one skilled in the art, all of which are in the spirit and purview of this invention.

What is claimed is:

1. An antiperspirant composition in the form of a transparent stick which is an oil-in-water emulsion comprising:
   (i) from 5 to 25% of an antiperspirant effective aluminum salt;
   (ii) from 10 to 40% of a nonionic surfactant which is a $C_{11}$–$C_{18}$ fatty alcohol alkoxylated with from about 10 to about 20 moles ethylene oxide;
   (iii) from 5 to 50% of a liquid oil immiscible with water; and
   (iv) from 20 to 50% water, and wherein said composition is free of any wax matrix.

2. An antiperspirant composition according to claim 1 wherein said liquid oil is selected from the group consisting of emollient oils, volatile silicones and mixtures thereof.

3. An antiperspirant composition according to claim 1 wherein said emollient oils are selected from the group consisting of linear and branched chain fatty acid ester, diesters of dicarboxylic acids, liquid hydrocarbons and mixtures thereof.

4. An antiperspirant composition according to claim 2 wherein said emollient oils are present in an amount from about 2 to 30% by weight.

5. An antiperspirant composition according to claim 2 wherein the emollient oils are present in an amount from about 5 to 15% by weight 6. An antiperspirant composition according to claim 2 wherein said emollient oil is 2-ethylhexyloxystearate.

7. An antiperspirant composition according to claim 2 wherein said volatile silicones are present in an amount from about 5 to 30% by weight.

8. An antiperspirant composition according to claim 2 wherein said volatile silicones are present in an amount from about 10% to 20% by weight.

9. An antiperspirant composition according to claim 2 comprising a mixture of volatile silicones and emollient oils in a ratio of from about 10:1 to 1:10.

10. An antiperspirant composition according to claim 2 wherein the ratio of volatile silicones to emollient oils ranges from about 4:1 to 1:4.

11. An antiperspirant composition according to claim 2 wherein the ratio of volatile silicones to emollient oils ranges from about 2:1 to 1:1.

12. An antiperspirant composition according to claim 1 wherein said liquid oil is a mixture of volatile silicone and 2-ethylhexyloxystearate in a ratio of about 2:1 to 1:1.

13. An antiperspirant composition according to claim 1 wherein the nonionic surfactant is a $C_{14}$–$C_{15}$ alcohol alkoxylated with about 13 moles ethylene oxide.

14. An antiperspirant composition according to claim 1 wherein the nonionic surfactant is present from about 25 to 35% by weight.

15. An antiperspirant composition according to claim 1 wherein the amount of water ranges from about 25 to 35% by weight.

16. An antiperspirant composition according to claim 1 wherein the aluminum salt is aluminum chlorohydrate.

17. An antiperspirant composition according to claim 1 wherein the amount of antiperspirant effective aluminum salt ranges from about 10 to 20% by weight.

* * * * *